(12) United States Patent
Shimizu et al.

(10) Patent No.: US 6,717,016 B2
(45) Date of Patent: Apr. 6, 2004

(54) PHOSPHINE COMPOUND, TRANSITION METAL COMPLEX CONTAINING THE SAME PHOSPHINE COMPOUND AS LIGAND AND ASYMMETRIC SYNTHESIS CATALYST CONTAINING THE COMPLEX

(75) Inventors: Hideo Shimizu, Hiratsuka (JP); Takao Saito, Hiratsuka (JP)

(73) Assignee: Takasago International Corporation, Tokyo (JP)

(*) Notice: Subject to any disclaimer, the term of this patent is extended or adjusted under 35 U.S.C. 154(b) by 0 days.

(21) Appl. No.: 10/330,495

(22) Filed: Dec. 30, 2002

(65) Prior Publication Data
US 2003/0144139 A1 Jul. 31, 2003

(30) Foreign Application Priority Data
Jan. 31, 2002 (JP) ......................... 2002-023568

(51) Int. Cl.$^7$ ................................. C07F 9/50
(52) U.S. Cl. .................. 568/12; 502/162; 556/13
(58) Field of Search ............... 568/8, 12; 556/13, 556/19, 20; 502/162, 166

(56) References Cited

FOREIGN PATENT DOCUMENTS

| DE | 1 282 633 B | 11/1968 |
| DE | 198 46 559 A1 | 4/2000 |
| WO | 91/17998 A1 | 11/1991 |
| WO | 93/01199 A1 | 1/1993 |

OTHER PUBLICATIONS

CA:100:191964 abs of Phosphorus and SUlfur and the Related Elements by Cowley et al 18 (1–1–3) pp 3–6 1983.*
CA:139:117446 abs of Science of Sythesis by Aitken, R. A. 10 pp 789–800 2001.*
CA:113:152575 abs of Chemistry Letters by Yoshifuji et al (5) pp 827–30 1990.*
CA:110:173322 abs of Phsphorus and Sulfur and Related Elements by Navech et al 35(3–4) pp 247–60 1988.*
Database Crossfire Beilstein; Abstract of Beilstein Registry No. 4935522; *J. Chem. Soc.*; pp. 2205; 1951.
Tsang, Chi–Wing, et al.; "Reactions of Electrophiles with the Phosphaalkene Mes*P═CH2:Mechanistic Studies of a Catalytic Intramolecular C–H Bond Activation Reaction"; *Organometallics*; vol. 21, No. 6, pp. 1008–1010; 2002.

* cited by examiner

Primary Examiner—Jean F. Vollano
(74) Attorney, Agent, or Firm—Kubovcik & Kubovcik

(57) ABSTRACT

A phosphine compound of formula (1)

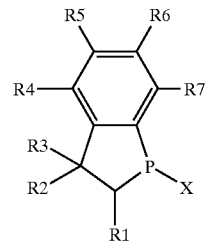

(1)

and a phosphine compound of formula (2)

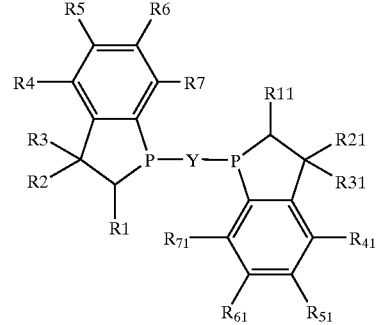

(2)

a transition metal complex having the phosphine compound as a ligand and a catalyst for asymmetric hydrogenation including the transition metal complex.

14 Claims, No Drawings

PHOSPHINE COMPOUND, TRANSITION METAL COMPLEX CONTAINING THE SAME PHOSPHINE COMPOUND AS LIGAND AND ASYMMETRIC SYNTHESIS CATALYST CONTAINING THE COMPLEX

BACKGROUND OF THE INVENTION

1. Field of the Invention

The present invention relates to a novel optically active phosphine compound, a transition metal complex including the same phosphine compound as a ligand and a transition metal catalyst useful for a variety of asymmetric synthetic reactions.

2. Description of the Related Art

There have hitherto been many reports on transition metal complexes which can be utilized for asymmetric syntheses such as asymmetric hydrogenations, asymmetric isomerizations, asymmetric hydrosilylations, asymmetric Heck reactions, asymmetric hydroborations and the like. Inter alia, complexes in which transition metal complexes such as ruthenium, rhodium, iridium, palladium and the like are coordinated with an optically active phosphine compound are potent catalysts for asymmetric reactions and some of the catalysts have been used for industrialization. (Asymmetric Catalysis in Organic Synthesis, Ed., R. Noyori, Wiley & Sons, New York (1994)). One of these ligands is a phospholane type compound. The phospholane compound when used as a ligand for a transition metal is useful for asymmetric syntheses such as asymmetric hydrogenations. (Document (A) WO91/17998, document (B) WO93/01199).

However, the phospholane type ligands described in documents (A) and (B) have an optically active phospholane ring structure, and a preparation of the phospholane ring needs expensive optically active 1,4-diols. The preparation of said 1,4-diols requires a special process and equipment (e.g., an electrochemical reaction such as a "Kolbe Reaction"), which makes industrialization difficult. Additionally, selectivities (diastereoselectivity, enantioselectivity) and catalytic activities of said phospholane ligands are not sufficient depending upon the reaction and reaction substrate and, thus, an improvement in a catalyst is occasionally demanded.

SUMMARY OF THE INVENTION

Accordingly, an object of the present invention is to provide a novel phosphine compound having excellent performance (diastereoselectivity, enantioselectivity, catalytic activity) as a ligand of catalysts for asymmetric reactions, in particular, asymmetric hydrogenation reactions. Furthermore, an object of the present invention is to provide an inexpensive preparation of the novel phosphine compound.

In order to achieve the above objects, the present inventors made extensive studies. As a result, it was found that a transition metal complex coordinated with a novel phosphine compound having a fused ring of a benzene ring and a phospholane ring is effective in an asymmetric hydrogenation reaction. It has also been found that this transition metal complex has excellent catalytic activity and enantioselectivity. The invention has been completed based on this finding.

PREFERRED EMBODIMENTS OF THE INVENTION

The present invention will be described in detail below.
One of the phosphine compounds of the present invention is represented by the following general formula (1):

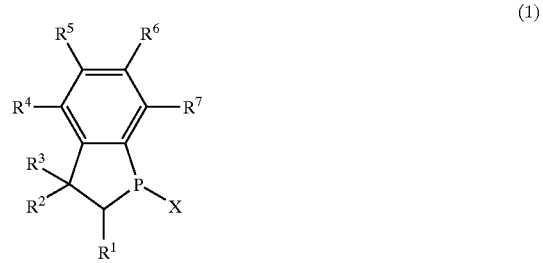

(1)

where $R^1$ is a linear or branched alkyl group having 1 to 5 carbon atoms, $R^2$ and $R^3$ represent independently a hydrogen atom or an alkyl group having 1 to 5 carbon atoms, $R^4$, $R^5$, $R^6$ and $R^7$ represent independently a hydrogen atom, a halogen atom, an alkyl group having 1 to 5 carbon atoms, an alkoxy group having 1 to 5 carbon atoms, a dialkylamino group where the alkyl has 1 to 5 carbon atoms, and X represents a functional group that forms a stable bond with a phosphorous atom, with the proviso that $R^4$ and $R^5$ or $R^5$ and $R^6$ or $R^6$ and $R^7$ taken together with the carbon atoms to which they are attached optionally form a ring or fused ring.

$R^1$ mentioned above includes a methyl group, ethyl group, n-propyl group, isopropyl group, n-butyl group, sec-butyl group, isobutyl group, tert-butyl group, n-pentyl group, isopentyl group, or neopentyl group.

As $R^2$ and $R^3$, groups such as a methyl group, ethyl group, n-propyl group, and isopropyl group are mentioned.

Examples of $R^4$, $R^5$, $R^6$, $R^7$ include a halogen atom such as fluorine, chlorine, bromine, and iodine; an alkyl group having 1 to 5 carbon atoms, such as a methyl group, ethyl group, n-propyl group, isopropyl group, n-butyl group, sec-butyl group, isobutyl group, tert-butyl group, n-pentyl group, isopentyl group, and neopentyl group; an alkoxy group having 1 to 5 carbon atoms, such as a methoxy group, ethoxy group, n-propoxy group, isopropoxy group, and tert-butoxy group; and a dialkylamino group where the alkyl has 1 to 5 carbon atoms, such as dimethylamino group, diethylamino group, pyrrolidino'group, and piperidino group.

Furthermore, the above-described ring or fused ring is a five to ten membered saturated or unsaturated ring such as a benzene ring, cyclopentene ring, cyclohexene ring, cyclopentadiene ring, indene ring, naphthalene ring, or heterocyclic ring such as a methylenedioxy ring system, ethylenedioxy ring system, or trimethylenedioxy ring system.

Specific examples of X are an alkyl group having 1 to 36 carbon atoms which may have a substituent, an aralkyl group, an aryl group which may have a substituent, a heterocyclic group, an alkoxy group, and an amino group. The substituent can be an alkyl group having 1 to 5 carbon atoms, an alkoxy group having 1 to 5 carbon atoms, a haloalkyl group having 1 to 5 carbon atoms, a halogen atom, an amino group, a mono alkylamino group and a dialkylamino group. Further, the alkyl group having 1 to 5 carbon atoms and alkoxy group having 1 to 5 carbon atoms can be any of those as described above.

Preferred specific examples of X are phenyl groups which may have a substituent, such as a phenyl group, 3-methoxyphenyl group, 3,4-methylenedioxyphenyl group, 1-naphthyl group, 2-naphthyl group, 3,5-di(tert-butyl)-4-methoxyphenyl group, 2-(diphenylphosphino) phenyl group, 2-(di(4-tolyl)phosphino)phenyl group, 2-(di(3,5-xylyl)phosphino)phenyl group, 2-(bis(3,5-di(tert-butyl)-4-methoxyphenyl)phosphino)phenyl group, 2-(di(1-naphthyl) phosphino)phenyl group, 2-(di(2-naphthyl)phosphino) phenyl group, 6-methoxy-2-(diphenylphosphino)phenyl group, and 5,6-methylenedioxy-2-(diphenylphosphino) phenyl group.

Another compound of the present invention is represented by the following general formula (2):

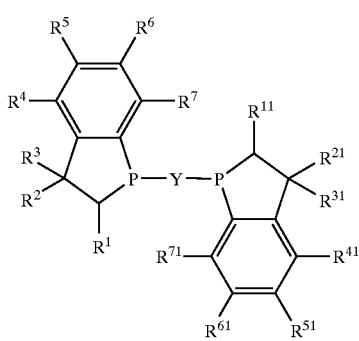

(2)

where $R^1$–$R^7$ are as defined above, $R^{11}$ is a linear or branched alkyl group having 1 to 5 carbon atoms, $R^{21}$ and $R^{31}$ represent independently a hydrogen atom or an alkyl group having 1 to 5 carbon atoms. $R^{41}$, $R^{51}$, $R^{61}$ and $R^{71}$ represent independently a hydrogen atom, a halogen atom, an alkyl group having 1 to 5 carbon atoms, an alkoxy group having 1 to 5 carbon atoms, a dialkylamino group where the alkyl has 1 to 5 carbon atoms, and Y represents a functional group that forms a stable bond with phosphorous with the proviso that $R^{41}$ and $R^{51}$ or $R^{51}$ and $R^{61}$ or $R^{61}$ and $R^{71}$ taken together with the carbon atoms to which they are attached optionally form a ring or a fused ring.

$R^{11}$ mentioned above includes a methyl group, ethyl group, n-propyl group, isopropyl group, n-butyl group, sec-butyl group, isobutyl group, tert-butyl group, n-pentyl group, isopentyl group, and neopentyl group.

As $R^{21}$ and $R^{31}$, groups such as a methyl group, ethyl group, n-propyl group, isopropyl group are mentioned.

Examples of $R^{41}$, $R^{51}$, $R^{61}$, $R^{71}$ include a halogen atom, such as fluorine, chlorine, bromine, and iodine; an alkyl group having 1 to 5 carbon atoms, such as a methyl group, ethyl group, n-propyl group, isopropyl group, n-butyl group, sec-butyl group, isobutyl group, tert-butyl group, n-pentyl group, isopentyl group, and neopentyl group; an alkoxy group having 1 to 5 carbon atoms, such as a methoxy group, ethoxy group, n-propoxy group, isopropoxy group, and tert-butoxy group; a dialkylamino group where the alkyl has 1 to 5 carbon atoms, such as a dimethylamino group, diethylamino group, pyrrolidino group, and piperidino group.

Furthermore, the above-described ring or fused ring is a five to ten membered saturated or unsaturated ring represented by a benzene ring, cyclopentene ring, cyclohexene ring, cyclopentadiene ring, indene ring, naphthalene ring, and heterocyclic ring including a methylenedioxy ring system, ethylenedioxy ring system, or trimethylenedioxy ring system.

Specific examples of Y are an alkylene group having 1 to 36 carbon atoms which may have substituent(s), an arylene group which may have substituent(s), a divalent heterocyclic group, —O—$R^{13}$—O—, —O—$R^{14}$—, —NR$^{23}$—$R^{15}$—, —NR$^{24}$—$R^{16}$—NR$^{25}$—, —NR$^{26}$—$R^{17}$—O—, (wherein $R^{13}$–$R^{17}$ represent independently an alkylene group having 1 to 36 carbon atoms which may have substituent(s), and an arylene group; and wherein $R^{23}$—$R^{26}$ represent independently a hydrogen atom and an alkyl group having 1 to 5 carbon atoms; and a divalent group having an alkylene structure and an arylene structure which may have substituent(s).

Specific examples of the divalent heterocyclic group are pyridine-2, 6-diyl (str. A) and phosphabenzene-2,6-diyl (str. B).

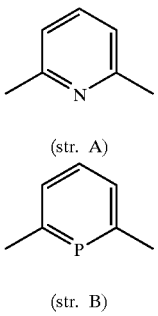

(str. A)

(str. B)

Further, specific examples of the divalent group having an alkylene structure and an arylene structure which may have substituent(s) are toluene-α,2-diyl group (str. C), ethylbenzene-β,2-diyl (str. D), o-xylene-α,α'-diyl (str. E).

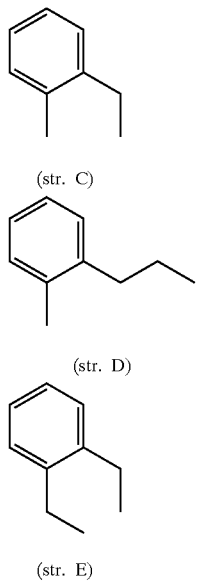

(str. C)

(str. D)

(str. E)

Preferred specific examples of Y are a phenylene group which may have substituent(s), and an alkylene group which may have substituent(s); more preferred examples are 1,2-phenylene group, 3-methoxy-1,2-phenylene group, 3,4-methylenedioxy-1,2-phenylene group, methylene group, ethylene group, trimethylene group, tetramethylene group, pentamethylene group, and hexamethylene group; and most preferred examples are 1,2-phenylene group, methylene group, and ethylene group.

The present invention includes racemic compounds, meso form compounds and optically active compounds of the aforementioned compounds. Preferred compounds of the aforementioned compounds are compounds where $R^2$, $R^3$, $R^{21}$, $R^{31}$ are a hydrogen atom, and more preferred compounds are compounds where $R^2$, $R^3$, $R^4$, $R^5$, $R^6$, $R^7$, $R^{21}$, $R^{31}$, $R^{41}$, $R^{51}$, $R^{61}$, $R^{71}$ are a hydrogen atom.

A process for preparing the compounds of the present invention will be described below. In order to avoid complexity, a representative embodiment of a process for preparing the present compounds is explained by referring to a optically active and (+)-form compound of the following formula (3) ((+)-1,2-bis(2-isopropyl-2,3-dihydro-1H-phosphindol-1-yl)benzene) (hereinafter referred to as "(+)-iPr-BeePHOS in some cases) among the compounds included in the present invention. However, the present invention is not limited thereto.

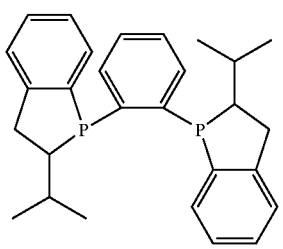

(3)

That is, 2-fluorophenylacetic acid (4) and 1,1'-carbonyldiimidazole (CDI) are reacted, followed by treatment with ethyl methylmalonate mono potassium salt in the presence of magnesium chloride to obtain ethyl 4-(2-fluorophenyl)-2-methyl-3-oxobutyrate (5).

The thus obtained compound (5) is asymmetrically hydrogenated using ((R)—SEGPHOS™)-Ru complex to obtain optically active ethyl 4-(2-fluorophenyl)-3-hydroxy-2-methylbutyrate (6) as a mixture of diastereomers.

(SEGPHOS):
((5,6),(5',6')-bis(methylenedioxy)biphenyl-2,2'-diyl) bis(di phenylphosphine))

Then, compound (6) is reduced with lithium aluminum hydride to obtain diol (7).

Further, the primary hydroxyl group of the diol (7) is tosylated, and reduction of the tosylate (8) with lithium aluminum hydride gives (+)-1-(2-fluorophenyl)-3-methylbutan-2-ol (9).

After alcohol (9) is mesylated to obtain mesylate (10), 1,2-bisphosphinobenzene is treated successively with n-butyl lithium, mesylate (10) and n-butyl lithium to obtain (+)-1,2-bis(2-isopropyl-2,3-dihydro-1H-phosphindol-1-yl) benzene (+)-(3) as a single diastereomer.

The compound (+)-(3) is produced by the process shown in the following reaction scheme 1.

[SCHEME 1]

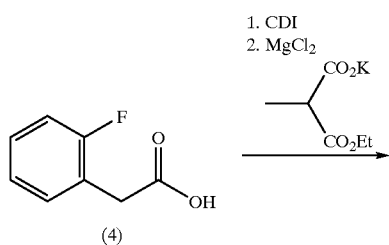

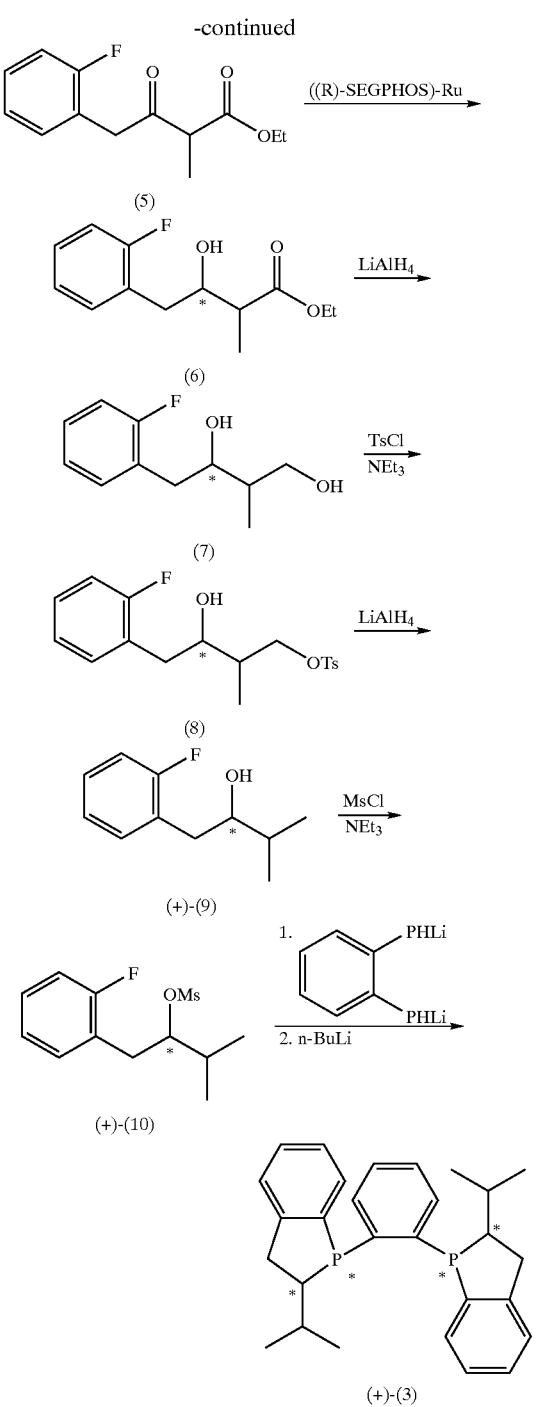

Ts = tosyl group, Ms = mesyl group
* represents an asymmetric carbon atom and aysmmetric phosphorous atom In addition, compound (−)-(3) can be obtained by using (S)-SEGPHOS™ instead of (R)-SEGPHOS™. Further, other optically active phosphine ligands may be used instead of SEGPHOS™. Furthermore, generally known transition metal complex for asymmetric synthesis can be used.

Among the present compounds, inter alia, the optically active compound (3) can be obtained from racemic compound (3) using HPLC equipped with an optically active column.

Further, optically active compound (3) can be obtained in a manner that racemic compound (3) is oxidized to the corresponding diphosphine oxide, the enantiomer is optically resolved by an optically active column, followed by reduction of the resolved diphosphine oxide with silane compound.

Additionally, optically active alcohol (9) can be obtained by optical resolution of racemic alcohol (9) by an enzyme.

Phosphines of the present invention represented by the general formula (1) may be obtained by using the corresponding primary phosphine instead of 1,2-bisphosphinobenzene in [SCHEME 1]. Examples of such corresponding primary phosphines are as follows:

Phenylphosphine, 3-methoxyphenylphosphine, 3,4-methylenedioxyphenylphosphine, 1-naphthylphosphine, 2-naphthylphosphine, 3,5-di(tert-butyl)-4-methoxyphenylphosphine 2-(diphenylphosphino)phenylphosphine, 2-(di(4-tolyl)phosphino)phenylphosphine, 2-(di(3,5-xylyl)phosphino)phenylphosphine, 2-(bis(3,5-di(tert-butyl)-4-methoxyphenyl)phosphino)phenylphosphine, 2-(di(1-naphthyl)phosphino)phenylphosphine, 2-(di(2-naphthyl)phosphino)phenylphosphine, 6-methoxy-2-(diphenylphosphino)phenylphosphine, and 5,6-methylenedioxy-2-(diphenylphosphino)phenylphosphine.

Phosphines of the present invention represented by the general formula (2) may be obtained by using the corresponding primary diphosphine instead of 1,2-bisphosphinobenzene in [SCHEME 1]. Examples of such corresponding primary diphosphines are as follows:

3-Methoxy-1,2-bisphosphinobenzene, 3,4-methylenedioxy-1,2-bisphosphinobenzene, 1,1-bisphosphinomethane, 1,2-bisphosphinoethane 1,3-bisphosphinopropane, 1,4-bisphosphinobutane, 1,5-bisphosphinopentane.

On the other hand, phosphines of the present invention represented by the general formula (1) or (2) may be obtained by using the corresponding alcohol instead of compound (9) in [SCHEME 1]. Examples of such corresponding alcohols are as follows:

1-(2-fluorophenyl)propane-2-ol;
1-(2-fluorophenyl)butan-2-ol;
3-(2-fluorophenyl)butan-2-ol;
3-(2-fluorophenyl)-3-methylbutan-2-ol;
2-(2-fluorophenyl)pentan-3-ol;
2-(2-fluorophenyl)-4-methylpentan-3-ol; and
2-(2-fluorophenyl)-2,4-dimethylpentan-3-ol.

Among the compounds of the invention, phosphine compounds represented by the general formula (1) or (2), and, in particular, the optically active compounds represented by the formula (1) or (2), are useful as a ligand of the transition metal complex of the present invention. The following will explain the transition metal complex of the invention. One of the transition metal complexes of the invention is represented by the general formula (31):

$$M_m L_n W_p U_q \quad (31)$$

(wherein M is transition metal selected from the group consisting of Ir, Rh, Ru, Pd and Ni, and L represents a phosphine compound of the present invention represented by the above general formula (1) as one molecule or two molecules, or a phosphine compound represented by the general formula (2): and with regard to W, U, m, n, p, and q, when M is Ir or Rh, W is Cl, Br, or I, and m=n=p=2 and q=0, when M is Ru, (i) W is Cl, Br, or I, U represents a trialkylamino, and m=n=2, p=4, and q=1, (ii) W is Cl, Br, or I, U represents a pyridyl group or a ring substituted pyridyl group, and m=n=1, p=2, and q=2, or (iii) W is a carboxylate group, and m=n=1, p=2, and q=0, (iv) W is Cl, Br, or I, and m=n=p=2 and q=0, or (v) W is Cl, Br or I and U represents a dialkyl ammonium ion, and m=n=2, p=5 and q=0, when M is Pd, (i) W is Cl, and m=n=1, p=2, and q=0 or (ii) W is allyl group, and m=n=p=2 and q=0, and when M is Ni, W is Cl, Br, or I, and m=n=1, p=2 and q=0)

In the above complex, the substituent for the pyridyl ring includes an alkyl group having 1 to 3 carbon atoms, a halogen atom, or the like. Moreover, the carboxylate group includes $CH_3COO$, $CH_3COCH_2COO$, and the like.

Another one of the transition metal complexes of the invention is represented by the general formula (32):

$$[M_m L_n W_p U_q]Z_s \quad (32)$$

(wherein M is a transition metal selected from the group consisting of Ir, Rh, Ru, Pd, and Ni and L represents a phosphine compound represented by the general formula (1) or (2); and with regard to W, U, Z, m, n, p, q, and s, when M is Ir, or Rh, W is 1,5-cyclooctadiene or norbornadiene, Z is $BF_4$, $ClO_4$, OTf, $PF_6$, $SbF_6$, or $BPh_4$, and m=n=p=s=1 and q=0, or m=1, n=2, p=q=0 and s=1, when M is Ru, (i) W is Cl, Br, or I, U represents an aromatic compound or olefin compound which is a neutral ligand, Z is Cl, Br, 1,13, or a sulfonate, and m=n=p=s=q=1 or (ii) Z is $BF_4$, $ClO_4$, OTf, $PF_6$, $SbF_6$, or $BPh_4$, and m=n=1, p=q=0, and s=2)

In the above complex, the aromatic compound as the neutral ligand includes benzene, p-cymene, or the like, and the olefin compound includes 1,5-cyclooctadiene, norbornadiene, or the like.

These transition metal complexes can be produced by a known method. By the way, with regard to the symbols used in the formulae shown in the following transition metal complexes, L represents an optically active compound among the compounds of the invention represented by the general formula (1) as one molecule or two molecules, or represented by the general formula (2) of the invention, cod represents 1,5-cyclooctadiene, nbd represents norbornadiene, Ph represents phenyl group, and Ac represents acetyl group.

Rhodium Complex:

As a specific example of producing a rhodium complex, the complex can be synthesized by reacting bis(cod)rhodium (I) tetrafluoroborate salt with phosphine compound (1) or (2) of the present invention according to the method described in "4 th edition Jikken Kagaku Koza (Lecture of Experimental Chemistry)" (Organic Metal Complexes, Vol. 18, pp. 339–344, 1991, edited by the Chemical Society of Japan, published by Marauzen).

The following can be mentioned as specific examples of the rhodium complex.

[Rh(L)Cl]$_2$, [Rh(L)Br]$_2$, [Rh(L)I]$_2$, [Rh(cod)(L)]OTf, [Rh(cod)(L)]BF$_4$, [Rh(cod)(L)]ClO$_4$, [Rh(cod)(L)]SbF$_6$, [Rh(cod)(L)]PF$_6$, [Rh(cod)(L)]BPh$_4$, [Rh(nbd)(L)]OTf, [Rh(nbd)(L)]BF$_4$, [Rh(nbd)(L)]ClO$_4$, [Rh(nbd)(L)]SbF$_6$, [Rh(nbd)(L)]PF$_6$, [Rh(nbd)(L)]BPh$_4$, [Rh(L)$_2$]ClO$_4$, [Rh(L)$_2$]OTf, [Rh(L)$_2$]BF$_4$, [Rh(L)$_2$]PF$_6$, [Rh(L)$_2$]SbF$_6$, [Rh(L)$_2$]BPh$_4$ Ruthenium Complex:

As the method for producing a ruthenium complex, for example, the complex can be prepared by heating [Ru(cod)Cl$_2$]$_n$ and BeePHOS under reflux in the presence of triethylamine in toluene solvent as described in the literature (T. Ikariya et al., J. Chem. Soc., Chem. Commun., 922(1988)). Moreover it can also be prepared by heating [Ru(p-cymene)I$_2$]$_2$ and BeePHOS under stirring in methylene chloride and ethanol according to the method described in the literature (K. Mashima et al, J. Chem. Soc., Chem. Commun., 1208 (1989)). The following can be mentioned as specific examples of the ruthenium complex.

Ru(OAc)$_2$(L), Ru(OCOCF$_3$)(L), Ru$_2$Cl$_4$(L)$_2$NEt$_3$, [{RuCl(L)}$_2$($\mu$-Cl)$_3$][Me$_2$NH$_2$], [{RuCl(L)}$_2$($\mu$-Br)$_3$][Me$_2$NH$_2$], [{RuCl(L)}$_2$($\mu$-I)$_3$][Me$_2$NH$_2$], [{RuCl(L)}$_2$($\mu$-Cl)$_3$][Et$_2$NH$_2$], [{RuCl(L)}$_2$($\mu$-Br)$_3$][Et$_2$NH$_2$], [{RuCl(L)}$_2$($\mu$-I)$_3$][Et$_2$NH$_2$], RuCl$_2$ (L), RuBr$_2$(L), RuI$_2$(L), RuCl$_2$(L)(pyridine)$_2$, RuBr$_2$(L)(pyridine)$_2$, RuI$_2$(L)(pyridine)$_2$, [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene) (L)]I, [Ru(L)](OTf)$_2$, [Ru(L)](BF$_4$)$_2$, [Ru(L)](ClO$_4$)$_2$, [Ru(L)](SbF$_6$)$_2$, [Ru(L)](BF$_4$)$_2$ Iridium Complex:

For example, the iridium complex can be prepared by reacting BeePHOS and an iridium compound, such as [Ir(cod)(CH$_3$CN)]BF$_4$ in tetrahydrofuran according to the method described in the literature (K. Mashima et al, J. Organomet. Chem., 428, 213 (1992)). The following can be mentioned as specific examples of the iridium complex.

[Ir(L)Cl]$_2$, [Ir(L)Br]$_2$, [Ir(L)I]$_2$, [Ir(cod)(L)]OTf, [Ir(cod)(L)]BF$_4$, [Ir(cod)(L)]ClO$_4$, [Ir(cod)(L)]SbF$_6$, [Ir(cod)(L)]PF$_6$, [Ir(cod)(L)]BPh$_4$, [Ir(nbd)(L)]OTf, [Ir(nbd)(L)]BF$_4$, [Ir(nbd)(L)]ClO$_4$, [Ir(cod)(L)]SbF$_6$, [Ir(nbd)(L)]PF$_6$, [Ir(nbd)(L)]BPh$_4$, IrCl(cod)(CO)(L), IrBr(cod)(CO)(L), IrI(cod)(CO)(L), [Ir(L)$_2$]ClO$_4$, [Ir(L)$_2$]OTf, [Ir(L)$_2$]BF$_4$, [Ir(L)$_2$]PF$_6$, [Ir(L)$_2$]SbF$_6$, [Ir(L)$_2$]BPh$_4$ Palladium Complex:

For example, the palladium complex can be prepared by reacting BeePHOS and a π-allylpalladium compound according to the method described in a literature (Y. Uozumi et al, J. Am. Chem. Soc., 113, 9887 (1991)). The following can be mentioned as specific examples of the palladium complex.

PdCl$_2$(L), PdBr$_2$(L), PdI$_2$(L), Pd(OAc)$_2$(L), Pd(OCOCF$_3$)$_2$(L), [(π-allyl)Pd(L)]Cl, [(π-allyl)Pd(L)]Br, [(π-allyl)Pd(L)]I, [(π-allyl)Pd(L)]OTf, [(π-allyl)Pd(L)]BF$_4$, [(π-allyl)Pd(L)]ClO$_4$, [(π-allyl)Pd(L)]SbF$_6$, [(π-allyl)Pd(L)]PF$_6$, [(π-allyl)Pd(L)]BPh$_4$, [Pd (L)](OTf)$_2$, [Pd(L)](BPh$_4$)$_2$, [Pd(L)](PF$_6$)$_2$, [Pd(L)](ClO$_4$)$_2$, [Pd(L)](BF$_4$)$_2$, [Pd(L)](SbF$_6$)$_2$, PhCH$_2$Pd(L)Cl, PhCH$_2$Pd(L)Br, PhCH$_2$Pd(L)I, PhPdCl(L), PhPdBr(L), PhPdI(L)

Nickel Complex:

The nickel complex can be prepared by the method described in "4 th edition Jikken Kagaku Koza (Lectured of Experimental Chemistry)", vol. 18, Organic Metal Complexes, 1991, Maruzen, p. 376, edited by the Chemical Society of Japan, or by dissolving BeePHOS and nickel chloride in a mixed solvent of 2-propanol and methanol and heating them under stirring according to the method described in a literature (Y. Uozumi et al, J. Am. Chem. Soc., 113, 9887 (1991)). The following can be mentioned as specific examples of the nickel complex. NiCl$_2$(L), NiBr$_2$(L), NiI$_2$(L)

The transition metal complex containing an optically active phosphine compound of the present invention as a ligand is a useful catalyst for asymmetric synthesis, such as asymmetric hydrogenation, asymmetric isomerization, asymmetric hydroformylation. Racemic modification of compound (1) and (2) is useful as an intermediate of the corresponding optically active compound. In the case of using the complex as a catalyst, the complex may be used after being purified or without purification thereof.

Thus, the novel phosphine compounds of the present invention are useful as, in particular, a ligand for a transition metal complex. Further, a transition metal complex containing said phosphine compound as a ligand is useful catalyst for asymmetric hydrogenation. This novel phosphine compound, useful as ligand, can be produced by a comparatively moderate method. In addition, an asymmetric hydrogenated product can be obtained with high yield and high optical purity by using this catalyst, and in an extremely industrially useful method.

The following Examples and Use Example further illustrate the present invention in detail but are not to be construed as limiting the scope thereof.

EXAMPLES

Apparatuses used for determining physical properties in the respective Examples are as follows:

Nuclear magnetic resonance: $^1$H-NMR Bruker AM400 (400 MHz)

$^{31}$P-NMR Bruker AM400 (202 MHz)

Optical rotation: Nihon Bunkoh Co., Ltd. DIP-4

Gas chromatography GLC: Hewlett Packard 5890-II

High-performance liquid chromatography HPLC: Hewlett Packard HP1100

Mass spectrometry (MS): M-80B manufactured by Hitachi

Example 1

Synthesis of (+)-1,2-bis(2-isopropyl-2,3-dihydrophosphoindole-1-yl)benzene ((+)-iPr-BeePHOS)

(a) Under a nitrogen stream, 20 g (129 mmol) of 2-fluorophenylacetic acid was dissolved in 30 ml of acetonitrile, and 23.0 (142 mmol) of 1,1'-carbonylbis-1H-imidazole (CDI) was added at room temperature. After the mixture was stirred for one hour, the obtained reaction solution was dropped into a suspension comprising 33.3 g (180 mmol) of potassium monoethyl methylmalonate, 14.7 g (155 mmol) magnesium chloride and 60 ml of acetonitrile, and then stirred overnight at 45° C. 200 ml of 1N hydrochloric acid was added to the reaction solution, and was extracted three times with 200 ml of ethyl acetate. The combined organic layer was washed with 100 ml of 1N hydrochloride, 100 ml of 5% sodium carbonate, and 200 ml of water (twice) and 200 ml of a saturated sodium chloride (brine) solution. The obtained reactant was dried by sodium sulfate anhydride, and solvent was removed. The residue was purified by silica gel column chromatography to obtain 23.1 g of the subject compound as colorless oil. (Yield: 95%)

$^1$H-NMR(CDCl$_3$): δ 1.27 (3H, t, J=7.2 Hz), 1.36 (3H, d, J=7.2 Hz), 3.64 (1H, q, J=7.2 Hz), 3.88 (2H, s), 4.18 (2H, q, J=7.2 Hz), 6.95–7.15 (4H, m)

EI-MS: m/z=238 (M+)

(b) Synthesis of ethyl 4-(2-fluorophenyl)-3-hydroxy-2-methylbutanoate 20.0 g (83.9 mmol) of ethyl 4-(2-fluorophenyl)-2-methyl-3-oxobutanoate, 138 mg (0.084 mmol) of [{RuCl(((R)-SEGPHOS))$_2$($\mu$-Cl)$_3$][Me$_2$NH$_2$], and 80 ml of ethanol were placed into a stainless autoclave, followed by stirring at a hydrogen pressure of 3.0 MPa at 80° C. for 18 hours. After the stirring, the solvent was distilled off and the residue was purified by silica gel column chromatography to obtain 18.6 g of the title compound as a colorless oil. (Yield: 93%). The title compound was analysed by gas chromatography (hereinafter, referred to as GC), and was 1:1 of a diastereomeric mixture, and the optical purities were 96.9% ee, 98.5% ee.

The diastereomeric rate and the optical purity were determined by Chirasil DEX CB as a conventional method.

EI-MS: m/z=241 (M+1)

(c) Synthesis of 4-(2-fluorophenyl)-3-hydroxy-2-methylbutane-1,3-diol

Under a nitrogen atmosphere, 2.84 g (74.9 mmol) of lithium aluminum hydride was added to 30 ml of tetrahydrofuran (hereinafter, referred to as THF). A solution of 18.0 g of ethyl 4-(2-fluorophenyl)-3-hydroxy-2-methylbutanoate in 180 ml of THF was added thereto. After stirring for 1.5 hr at room temperature, 5 ml of water and 5 ml of 1N-NaOH aqueous solution were added thereto successively to quench the reaction. 100 ml of $Et_2O$ was added to the quenched reaction mixture, after stirring a while, the obtained suspension was filtered. The filtrate was distilled off and the residue was purified by silica gel column chromatography to obtain 14.5 g of the title compound as a colorless oil. (Yield: 99%)

EI-MS m/z 199 (M+1)

(d) Synthesis of 4-(2-fluorophenyl)-3-hydroxy-2-methylbutyl Tosylate

Under a nitrogen atmosphere, a mixture of 13.5 g (68.1 mmol) of 4-(2-fluorophenyl)-3-hydroxy-2-methylbutane-1,3-diol, 14.2 ml (21.3 mmol) of triethylamine, and 70 ml of dichloromethane was cooled with an ice bath and 13.0 g (68.1 mmol) of p-toluenesufonyl chloride was added to the mixture. After stirring overnight at room temperature, 100 ml of water was added thereto, followed by extraction 3 times each with 200 ml of dichloromethane, and the combined organic layer was dried with anhydrous sodium sulfate. After drying, the solvent was distilled off and the residue was purified by silica gel column chromatography to obtain 21.1 g of the title compound as a colorless oil. (Yield: 88%)

EI-MS m/z 353 (M+1)

(e) Synthesis of (+)-1-(2-fluorophenyl)-3-methylbutane-2-ol

Under a nitrogen atmosphere, 2.28 g (60.2 mmol) of lithium aluminum hydride was added to 30 ml of THF. A solution of 21.1 g (60.2 mmol) of 4-(2-fluorophenyl)-3-hydroxy-2-methylbutyl tosylate in 210 ml of THF was added dropwise thereto at room temperature. After stirring for 0.5 hr at room temperature, sodium sulfate 10 hydrate was added slowly until no effervescence was observed. After stirring a while, the obtained suspension was filtered, the filtrate was distilled off and the residue was purified by silica gel column chromatography to obtain 9.6 g of the title compound as a colorless solid. (Yield: 88%) An optical purity was determined to be 98.1% ee by GC using Chirasil DEX CB according to a conventional method.

$^1$H-NMR ($CDCl_3$): δ 1.01 (6H, d, J=6.6 Hz), 1.76 (1H, dqq, J=5.5, 6.6, 6.6 Hz), 2.63 (1H, dd, J=9.3, 13.2 Hz), 2.92 (1H, dd, J=2.7, 13.2 Hz), 3.64 (1H, m), 7.00–7.10 (2H, m), 7.18–7.28 (2H, m)

$[α]_D^{24}$:+27.9 (c 1.0, $CHCl_3$)

EI-MS: m/z=182 (M+)

(f) Synthesis of (+)-1-(2-fluorobenzyl)-2-methylpropyl Mesylate (Hereinafter Referred to as "MESYLATE" in Some Cases)

Under a nitrogen atmosphere, a mixture of 8.6 g (47.2 mmol) of (+)-1-(2-fluorophenyl)-3-methylbutane-2-ol, 7.9 ml (56.6 mmol) of triethylamine, and 40 ml of dichloromethane was cooled with an ice bath, and 4.0 ml (51.9 mmol) of methanesufonyl chloride was added dropwise to the mixture. After the dropping, the ice bath was removed and stirred overnight at room temperature. 100 ml of water was added thereto, followed by extraction 3 times each with 100 ml of dichloromethane, and the combined organic layer was washed with 100 ml of brine, and dried with anhydrous sodium sulfate. After drying, the solvent was distilled off and the residue was purified by silica gel column chromatography to obtain 12.5 g of the title compound. (Yield: 91%)

$^1$H-NMR ($CDCl_3$): δ 1.06 (3H, d, J=7.0 Hz), 1.08 (3H, d, J=7.0 Hz), 2.07 (1H, dqq, J=4.2, 7.0, 7.0 Hz), 2.48 (3H, s), 2.93 (1H, dd, J=9.0, 14.6 Hz), 3.06 (1H, dd, J=4.4, 14.6 Hz), 4.77 (1H, ddd, J=4.2, 4.4, 9.0 Hz), 6.98–7.15 (2H, m), 7.18–7.32 (2H, m)

$[α]_D^{24}$: +30.8 (c 1.0, $CHCl_3$)

(g) Synthesis of (+)-1,2-bis(2-isopropyl-2,3-dihydro-1H-phosphindol-1-yl)benzene ((+)-iPr-BeePHOS)

Under a nitrogen atmosphere, 300 μl (2.32 mmol) of 1,2-bisphosphinobenzene was added to 9 ml of THF, followed by cooling with an ice bath. Then, a 1.6M solution of 2.9 ml (4.64 mmol) of n-butyllithium in hexane was added dropwise thereto and, after dropping, the mixture was stirred for 1 hr, and 1.21 g (4.64 mmol) of MESYLATE in 12 ml of THF solution was added dropwise thereto, stirred for 1 hr and, after removing ice bath, the mixture was stirred for 1 hr at room temperature. Following recooling with an ice bath, a 1.6M solution of 4.4 ml (6.96 mmol) of n-butyllithium in a hexane solution was added dropwise thereto and, after dropping, the ice bath was removed and the mixture was stirred overnight at room temperature. 1 ml of water was added to the reaction mixture to quench the reaction and the solvent was distilled off. 10 ml of water was added to the residue followed by extraction 2 times each with 20 ml of $Et_2O$, and the combined organic layer was washed with 10 ml of water, the solvent was distilled off and the residue was purified by silica gel column chromatography to obtain 227 mg of the title compound. (Yield: 23%) m.p.: 70–71° C.

$^1$H-NMR ($CDCl_3$): δ 1.05 (6H, d, J=6.4 Hz), 1.09 (6H, d, J=6.8 Hz), 2.09–2.21 (2H, m), 2.60–2.69 (2H, m), 2.93–3.01 (2H, m), 3.28–3.36 (2H, m), 6.74–6.80 (2H, m), 7.02–7.06 (2H, m), 7.18–7.40 (8H, m)

$^{31}$P-NMR ($CDCl_3$): δ +0.20 (s)

$[α]_D^{24}$:+186.1 (c 1.0, $CHCl_3$)

HRMS: 430.1960 (calcd. 430.1978)

Example 2

Synthesis of (+)-1-(2-diphenylphosphinophenyl)-2-isopropyl-2,3-dihydro-1H-phosphindol-1-yl)benzene ((+)-m-iPr-BeePHOS)

Under a nitrogen atmosphere, 1.0 g (3.40 mmol) of 2-(diphenylphosphino)phenylphosphine was added to 30 ml of THF, followed by cooling with an ice bath. Then, a 1.6M solution of 2.1 ml (3.40 mmol) of n-butyllithium in hexane was added dropwise thereto and, after dropping, the mixture was stirred for 1 hr, a solution of 885 mg(3.40 mmol) of MESYLATE in 10 ml of THF was added dropwise thereto, stirred for 1 hr and, after removing the ice bath, the mixture was stirred for 1 hr at room temperature. Following recooling with an ice bath, a 1.6M solution of 3.2 ml (5.10 mmol) of n-butyllithium in hexane was added dropwise thereto and, after dropping, the ice bath was removed and the mixture was stirred overnight at room temperature. 1 ml of water was added to the reaction mixture to quench the reaction and the solvent was distilled off. 10 ml of water was added to the residue and extracted 3 times each with 20 ml of $Et_2O$, and the combined organic layer was washed with 10 ml of water, the solvent was distilled off and the residue was purified by silica gel column chromatography to obtain 400 mg of the title compound. (Yield: 27%)

m.p.: 41–42° C.

$^1$H-NMR (CDCl$_3$): δ 1.81 (3H, d, J=6.6 Hz), 0.83 (3H, d, J=6.6 Hz), 1.81 (1H, qqd. J=6.6, 6.6, 8.8 Hz), 2.20–2.28 (1H, m), 2.85 (1H, ddd, J=4.9, 4.9, 16.5 Hz), 3.24 (1H, ddd, J=4.4, 8.2, 16.5 Hz), 6.80–6.85 (1H, m), 6.93–6.98 (1H, m), 7.10–7.40 (3H, m), 7.20–7.40 (13H, m)

$^{31}$P-NMR (CDCl$_3$): δ −12.9 (d, J=147.5 Hz), −0.4 (d, J=147.5 Hz)

$[α]_D^{24}$:+84.7 (c 1.0, CHCl$_3$)

HRMS: 438.1597 (calcd. 438.1665)

Example 3

Synthesis of (+)-1-(2-bis(3,5-di-tert-butyl-4-methoxyphenyl)phosphinophenyl)-2-isopropyl-2,3-dihydro-1H-phosphindol ((+)-DTBM-iPr-BeePHOS)

Under a nitrogen atmosphere, 1.0 g (1.72 mmol) of 2-(bis(3,5-di(tert-butyl)-4-methoxyphenyl)phosphino)phenylphosphine was added to 30 ml of THF, followed by cooling with an ice bath. Then, a 1.6M solution of 1.1 ml (1.72 mmol) of n-butyllithium in hexane was added dropwise thereto and, after dropping, the mixture was stirred for 1 hr, a solution of 448 mg (1.72 mmol) of MESYLATE in 10 ml of THF was added dropwise thereto, stirred for 1 hr and, after removing the ice bath, the mixture was stirred for 1 hr at room temperature. Following recooling with an ice bath, a 1.6M solution of 1.6 ml (2.58 mmol) of n-butyllithium in hexane was added dropwise thereto, after dropping, the ice bath was removed and the mixture was stirred overnight at room temperature. 1 ml of water was added to the reaction mixture to quench the reaction and the solvent was distilled off. 10 ml of water was added to the residue and extracted 3 times each with 20 ml of Et$_2$O, and the combined organic layer was washed with 10 ml of water, the solvent was distilled off and the residue was purified by silica gel column chromatography to obtain 337 mg of the title compound. (Yield: 27%)

m.p.: 69–70° C.

$^1$H-NMR (CDCl$_3$): δ 0.69 (3H, d, J=6.6 Hz), 0.71 (3H, d, J=6.6 Hz), 1.29–1.34 (36H, m), 1.63–1.73 (1H, m), 2.00–2.06 (1H, m) 2.78–2.86 (1H, m) 3.12–3.21 (1H, m), 3.67 (3H, s), 3.69 (3H, s), 6.75–6.80 (1H, m), 6.87–6.92 (1H, m), 7.02–7.30 (9H, m), 7.31–7.35 (1H, m)

$^{31}$P-NMR (CDCl$_3$): δ °C. −13.9(d, J=145.4 Hz), −1.4 (d, J=145.4 Hz)

$[α]_D^{24}$:+8.45 (c 1.0, CHCl$_3$)

HRMS: 722.4397 (calcd. 722.4382)

Example 4

Synthesis of (+)-1,2-bis(2-methyl-2,3-dihydro-1H-phosphindol-1-yl)benzene ((+)-BeePHOS)

(a) Synthesis of 2-(2-fluorophenyl)ethanol

Under a nitrogen atmosphere, a solution of 10 g (64.9 mmol) of 2-fluorophenylacetic acid in 100 ml of THF was slowly added to a suspension of 2.46 g (64.0 mmol) of lithium aluminum hydride in 50 ml of THF at room temperature. After stirring for 1 hr, sodium sulfate 10-hydrate was slowly added until no effervescence was observed. The reaction mixture was filtered and the filtrate was distilled off to obtain 8.83 g of the title compound (Yield: 97%).

$^1$H NMR (CDCl$_3$): δ 1.48 (1H, bs), 2.93 (2H, t, J=6.6 Hz), 3.87 (2H, td, J=6.6, 6.6 Hz), 6.95–7.40 (4H, m);

EI-MS: m/z 140 (M)$^+$ (b) Synthesis of 2-(2-fluorophenyl)ethyl Diisopropylcarbamate Under a nitrogen atmosphere, a mixture of 8.0 g (57.1 mmol) of 2-(2-fluorophenyl)ethanol, 9.34 g (57.1 mmol) of diisopropylcarbamoyl chloride and 6.93 ml (85.7 mmol) of pyridine was heated to 90° C. and stirred overnight. After cooling to room temperature, the mixture was treated with 1 N—HCl, extracted 3 times with ethyl acetate, washed with water, saturated NaHCO$_3$, water and brine and then dried over sodium sulfate. After the solvent was distilled off, purification of the residue by silica gel chromatography gave 14.0 g of the title compound. (Yield: 98%).

$^1$H NMR (CDCl$_3$): δ 1.14 (12H, d, J=6.8 Hz), 3.01 (2H, t, J=6.8 Hz), 3.50–4.20 (2H, m), 4.31 (2H, t, J=6.8 Hz), 6.95–7.30 (4H, m);

EI-MS: m/z 267 (M)$^+$ (c) Synthesis of 2-(2-fluorophenyl)-1-methylethyl Diisopropylcarbamate Under a nitrogen atmosphere, a solution of 14.1 g (60.2 mmol) of (−)-Sparteine in 75 ml of diethyl ether was cooled to −78° C. and a 1.0M solution of 60.2 ml (60.2 mmol) of s-butyllithium in cyclohexane was added dropwise. The reaction mixture was stirred for 15 min and then added to a solution of 10 g (40.1 mmol) of 2-(2-fluorophenyl)ethyl diisopropylcarbamate in diethyl ether at −78° C. After stirring for 4 hr, methyl iodide was added, followed by stirring for 2 hr. Water was added and the resulting mixture was warmed to room temperature. The mixture was treated with 1 N—HCl, extracted 3 times with ethyl acetate, washed with water and brine and then dried over sodium sulfate. After the solvent was distilled off, purification of the residue by silica gel column chromatography gave 5.11 g of the title compound. (Yield: 45%).

$^1$H NMR (CDCl$_3$): δ 1.16 (12H, d, J=6.8 Hz), 1.25 (3H, d, J=6.4 Hz), 2.80–3.10 (2H, m), 3.60–4.15 (2H, m), 5.12 (1H, tq, J=6.4, 6.8 Hz), 6.90–7.30 (4H, m).

(d) Synthesis of (+)-1-(2-fluorophenyl)propan-2-ol

Under a nitrogen atmosphere, to a solution of 5.11 g (18.2 mmol) of 2-(2-fluorophenyl)-1-methylethyl diisopropylcarbamate in THF, a 1.0M solution of 182 ml (182 mmol) of diisobutylaluminum hydride in THF was added dropwise. The reaction mixture was stirred overnight at room temperature and sodium sulfate 10-hydrate was slowly added until no effervescence was observed. After addition of the sodium sulfate, the mixture was filtered, the filtrate was distilled off and purified by silica gel column chromatography, giving 2.15 g of the title compound. (Yield: 77% yield, 97% ee)

The optical purity (% ee) was determined by GC (Chirasil DEX-CB).

$[α]_D^{24}$: +27.3 (c 1.0, CHCl$_3$);

$^1$H NMR (CDCl$_3$): δ 1.25 (3H, d, J=6.2 Hz), 1.50 (1H, d, J=4.4 Hz), 2.74 (1H, ddd, J=1.0, 7.4, 13.4 Hz), 2.86 (1H, ddd, J=1.2, 5.2, 13.4 Hz), 3.95–4.20 (1H, m), 6.95–7.35 (4H, m);

EI-MS: m/z 154 (M)$^+$ (e) Synthesis of (+)-2-(2-fluorophenyl)-1-methylethyl Mesylate Under a nitrogen atmosphere, to a mixture of 2.15 g (14.0 mmol) of (+)-1-(2-fluorophenyl)-propan-2-ol and 2.34 ml (16.8 mmol) of triethylamine in 10 ml of dichloromethane, 1.19 ml (15.4 mmol) of methanesulfonyl chloride was added at 0° C. The resulting mixture was stirred overnight at room temperature and then treated with water and extracted 3 times with dichloromethane. The combined organic layer was then washed with water, solvent was distilled off and the residue was purified by silica gel chromatography, giving 2.68 g of the title compound. (Yield: 82%).

$[\alpha]_D^{24}$: +23.4 (c 1.0, CHCl$_3$);

$^1$H NMR (CDCl$_3$): δ 1.48 (3H, d, J=6.6 Hz), 2.62 (3H, s), 2.90–3.10 (2H, m), 4.95 (1H, qt, J=6.6, 6.6 Hz), 6.95–7.40 (4H, m).

(f) Synthesis of (+)-1,2-bis(2-methyl-2,3-dihydroxy-1H-phosphindol-1-yl)benzene (Hereinafter Referred to as (+)-BeePHOS)

367 mg of the title compound was obtained in a similar manner to Example 1(g) from 1.80 g (7.74 mmol) of (+)-2-(2-fluorophenyl)-1-methylethyl mesylate which was used instead of MESYLATE. (Yield: 25%).

Mp: 148–150° C.;

$[\alpha]_D^{24}$: +301.1 (c 1.0, CHCl$_3$);

$^1$H NMR (CDCl$_3$): δ 1.42 (6H, dd, J=7.7, 19.8 Hz), 2.74–2.81 (2H, m) 2.93 (2H, ddq, J=2.7, 7.7, 7.7 Hz), 3.33–3.40 (2H, m), 6.53–6.60 (2H, m), 6.95–7.05 (2H, m), 7.26–7.32 (2H, m), 7.37–7.45 (2H, m), 7.56–7.60 (2H, m);

$^{31}$P NMR (CDCl$_3$): δ 10.3;

HRMS: m/z 374.1321 (calc. 374.2353 for C$_{24}$H$_{24}$P$_2$).

Example 5

Synthesis of (+)-1-(2-Diphenylphosphinophenyl)-2-methyl-2,3-dihydro-1H-phosphindole (Hereinafter Referred to as (+)-m-BeePHOS)

The same procedure as Example 2 was used except that 738 mg (3.18 mmol) of (+)-2-(2-fluorophenyl)-1-methylethyl mesylate was used instead of MESYLATE, giving 686 g of the title compound (Yield: 53%).

Mp: 40–42° C.;

$[\alpha]_D^{24}$: +55.1 (c 1.0, CHCl$_3$);

$^1$H NMR (CDCl$_3$): δ 1.06 (3H, dd, J=7.1, 20.0 Hz), 2.10–2.30 (1H, m), 2.63 (1H, ddd, J=3.0, 6.8, 16.2 Hz), 3.31 (1H, ddd, J=2.4, 7.6, 16.2 Hz), 6.65–6.70 (1H, m), 6.98–7.03 (1H, m), 7.07–7.12 (1H, m), 7.15–7.19 (1H, m), 7.28–7.40 (13H, m), 7.49–7.53 (1H, m);

$^{31}$P NMR (CDCl$_3$): δ −13.6 (d, J=147.8 Hz), 7.7 (d, J=147.8 Hz);

HRMS: m/z 410 (M)$^+$.

Example 6

Preparation of [Rh(cod)((+)-ipr-BeePHOS)]OTf

Under an argon atmosphere, 54.3 mg (0.116 mmol) of [Rh(cod)$_2$]OTf was dissolved into 5 ml of dichloromethane in a 20 ml Schlenk tube, and then 2.5 ml of a dichloromethane solution of 50 mg (0.116 mmol) of (+)-iPrBeePHOS was added thereto at room temperature. After stirring overnight, the solvent was removed and the residue was recrystallised from dichloromethane (0.5 ml)-diethyl ether (5 ml), and thereafter the precipitate was filtered off, washed twice each with 5 ml of diethyl ether, and vacuum dried to obtain 73.8 mg of the title compound. (Yield: 81%).

$^1$H NMR (CD$_2$Cl$_2$): δ 1.18 (6H, d, J=6.6 Hz), 1.22 (6H, d, J=6.6 Hz), 2.17–2.36 (8H, m), 2.47–2.55 (2H, m), 2.88–2.99 (2H, m), 3.11–3.17 (2H, m), 3.68–3.78 (2H, m), 5.03–5.10 (2H, m), 5.14–5.20 (2H, m), 7.11–7.15 (2H, m), 7.32–7.41 (4H, m), 7.47–7.54 (4H, m), 7.58–7.63 (2H, m);

$^{31}$P NMR (CD$_2$Cl$_2$): δ 73.4 (d, J=151.5 Hz)

Example 7

Preparation of [Rh(cod)((+)-m-iPr-BeePHOS)]OTf 79.3 mg of the title compound was obtained in a similar manner to Example 6 from 50 mg (0.114 mmol) of (+)-m-iPr-BeePHOS with 53.4 mg (0.114 mmol) of [Rh(cod)$_2$]OTf. (Yield: 87%)

$^1$H NMR (CD$_2$Cl$_2$): δ 0.75 (3H, d, J=6.6 Hz), 1.05 (3H, d, J=6.6 Hz), 1.93–2.12 (3H, m), 2.17–2.34 (4H, m), 2.36–2.46 (2H, m), 2.86–2.95 (1H, m), 2.99–3.05 (1H, m), 3.59 (1H, ddd, J=8.23, 16.5, 22.5 Hz), 4.83–4.93 (2H, m), 5.09–5.15 (1H, m), 5.21–5.28 (1H, m), 7.06–7.11 (1H, m), 7.28–7.36 (2H, m), 7.40–7.56 (12H, m), 7.56–7.65 (3H, m);

$^{31}$P NMR (CD$_2$Cl$_2$): δ 60.8 (dd, J=25.6, 151.5 Hz), 72.2 (dd, J=25.6, 145.1 Hz).

Example 8

Preparation of [Rh (cod) ((+)-DTBM-ipr-BeePHOS)]OTf 75.0 mg of the title compound was obtained in a similar manner to Example 6 from 50 mg (0.069 mmol) of (+)-DTBM-iPr-BeePHOS with 32.4 mg (0.069 mmol) of [Rh (cod)$_2$]OTf except for washing 3 times each with 5 ml of hexane instead of purification by dichloromethane-diethylether. (Yield: 100%)

$^1$H NMR (CD$_2$Cl$_2$): δ 0.85 (3H, d, J=6.6 Hz), 1.11 (3H, d, J=6.6 Hz), 1.36 (18H, s), 1.37 (18H, s), 2.03–2.20 (3H, m), 2.25–2.39 (4H, m), 2.43–2.50 (2H, m), 2.95–3.11 (2H, m), 3.65 (1H, ddd, J=7.1, 15.9, 22.5 Hz), 4.87–4.94 (1H, m), 4.94–5.00 (1H, m), 5.11–5.18 (1H, m), 5.33–5.40 (1H, m), 7.10–7.14 (1H, m), 7.28–7.36 (3H, m), 7.40–7.46 (1H, m), 7.46–7.53 (4H, m), 7.55–7.64 (3H, m); $^{31}$P NMR (CD$_2$Cl$_2$): δ 62.0 (dd, J=25.6, 149.4 Hz), 70.5 (dd, J=25.6, 147.3 Hz)

Example 9

Preparation of [Rh(cod) ((+)-BeePHOS)]OTf 81 mg of the title compound was obtained in a similar manner to Example 6 from 42 mg (0.114 mmol) of (+)-BeePHOS with 53.4 mg (0.114 mmol) of [Rh(cod)$_2$]OTf. (Yield: 98%)

$^1$H NMR (CD$_2$Cl$_2$): δ 1.52–1.60 (6H, m), 2.17–2.38 (6H, m), 2.48–2.57 (2H, m), 3.05–3.20 (4H, m), 3.65–3.75 (2H, m), 5.08–5.16 (2H, m), 5.16–5.23 (2H, m), 7.23–7.30 (2H, m), 7.36–7.44 (4H, m), 7.48–7.52 (2H, m), 7.52–7.59 (2H, m), 7.60–7.65 (2H, m);

$^{31}$P NMR (CD$_2$Cl$_2$): δ 81.3 (d, J=151.2 Hz).

Example 10

Preparation of [Rh(cod)((+)-m-BeePHOS)]OTf 85 mg of the title compound was obtained in a similar manner to Example 6 from 46 mg (0.114 mmol) of (+)-m-BeePHOS with 53.4 mg (0.114 mmol) of [Rh(cod)$_2$]OTf. (Yield: 98%)

$^1$H NMR (CD$_2$Cl$_2$): δ 1.30 (3H, dd, J=7.1, 19.8 Hz), 2.04–2.60 (8H, m), 2.84–2.95 (1H, m), 2.98–3.03 (1H, m), 3.61 (1H, ddd, J=8.2, 17.0, 18.7 Hz), 4.71–4.78 (1H, m), 4.90–4.98 (1H, m), 5.29–5.41 (2H, m), 7.22–7.27 (2H, m), 7.37–7.41 (2H, m), 7.43–7.75 (14H, m); $^{31}$P NMR (CD$_2$Cl$_2$): δ 60.5 (dd, J=27.7, 151.5 Hz), 78.2 (dd, J=27.7, 149.4 Hz).

Example 11

Preparation of [RuCl (p-cymene) ((+)-iPr-BeePHOS)]Cl

Under an argon atmosphere, 71.0 mg (0.116 mmol) of [RuCl$_2$(p-cymene)]$_2$ was dissolved into 2.5 ml of dichloromethane and 2.5 ml of ethanol in a 20 ml Schlenk tube, and 100 mg (0.232 mmol) of (+)-iPr-BeePHOS was added thereto and stirred overnight at 50° C. After stirring, the solvent was distilled off and the residue was washed 3 times each with 5 ml of diethylether, and vacuum dried to obtain 165 mg of the title compound. (Yield: 97%).

$^1$H NMR (CD$_2$Cl$_2$): δ 0.50 (3H, d, J=6.6 Hz), 0.53 (3H, d, J=6.6 Hz), 1.01 (3H, d, J=6.6 Hz), 1.02 (3H, d, J=6.6 Hz), 1.14 (3H, d, J=7.1 Hz), 1.23 (3H, d, J=7.1 Hz), 1.62 (3H, s), 2.06–2.17 (1H, m), 2.37 (1H, qq, J=7.1, 7.1 Hz), 2.64–2.80 (2H, m), 3.00–3.08 (1H, m), 3.47–3.67 (3H, m), 3.76 (1H, ddd, J=8.2, 10.4, 17.0 Hz), 5.90–5.95 (1H, m), 6.07–6.11 (1H, m), 6.12–6.17 (1H, m), 6.31–6.36 (1H, m), 7.10–7.16 (1H, m), 7.24–7.34 (2H, m), 7.34–7.40 (1H, m), 7.42–7.50 (2H, m), 7.52–7.60 (4H, m), 7.60–7.65 (1H, m), 7.76–7.81 (1H, m); $^{31}$P NMR (CD$_2$Cl$_2$): δ 87.1 (d, J=36.3 Hz), 92.3 (d, J=36.3 Hz).

Example 12

Preparation of [RuCl(p-cymene) ((+)-m-ipr-BeePHOS)]Cl 80 mg of the title compound was obtained in a similar manner to Example 11 from 46 mg (0.232 mmol) of (+)-m-iPr-BeePHOS with 71.0 mg (0.116 mmol) of [RuCl$_2$(p-cymene)]$_2$. (Yield: 98%)

$^{31}$P NMR (CD$_2$Cl$_2$): major δ 68.6 (d, J=36.3 Hz), 82.3 (d, J=36.3 Hz), minor δ 68.6 (d, J=36.3 Hz), 84.3 (d, J=36.3 Hz).

Example 13

Preparation of [RuCl(p-cymene) ((+)-BeePHOS)]Cl 71 mg of the title compound was obtained in a similar manner to Example 11 from 87 mg (0.232 mmol) of (+)-BeePHOS with 71.0 mg (0.116 mmol) of [RuCl$_2$(p-cymene)]$_2$. (Yield: 97%)

$^1$H NMR (CD$_2$Cl$_2$): δ 0.76 (3H, d, J=7.1 Hz), 0.89 (3H, d, J=7.1 Hz), 1.49 (3H, dd, J=7.1, 18.7 Hz), 1.50 (3H, s), 1.64 (3H, dd, J=7.1, 19.8 Hz), 2.21 (1H, qq, J=7.1, 7.1 Hz), 3.07–3.19 (1H, m), 3.19–3.27 (1H, m), 3.33 (1H, ddd, J=3.8, 10.4, 17.6 Hz), 3.56–3.70 (2H, m), 4.05 (1H, ddd, J=7.7, 7.7, 17.6 Hz), 5.75–5.81 (1H, m), 5.94–6.00 (1H, m), 6.31–6.37 (1H, m), 6.49–6.57 (1H, m), 7.21–7.31 (2H, m), 7.32–7.41 (2H, m), 7.42–7.53 (3H, m), 7.53–7.61 (4H, m), 7.78–7.85 (1H, m); $^{31}$P NMR (CD$_2$Cl$_2$): δ 86.3 (d, J=36.3 Hz), 95.1 (d, J=36.3 Hz).

Example 14

Preparation of [RuCl(p-cymene)((+)-m-BeePHOS)]Cl 77 mg of the title compound was obtained in a similar manner to Example 11 from 95 mg (0.232 mmol) of (+)-m-BeePHOS with 71.0 mg (0.116 mmol) of [RuCl$_2$(p-cymene)]$_2$. (Yield: 98%)

$^{31}$P NMR (CD$_2$Cl$_2$): major δ 67.7 (d), 88.8 (d), minor δ 66.9 (d), 81.9 (d).

Example 15

Preparation of Ru(OAc)$_2$((+)-iPr-BeePHOS)

Under an argon atmosphere, 100 mg (0.136 mmol) of [RuCl(p-cymene)(+)-iPr-BeePHOS]Cl and 27.9 mg (0.34 mmol) of sodium acetate were dissolved into 5 ml of dioxane in 20 ml Schlenk tube The mixture was stirred overnight at 100° C. and then cooled to room temperature followed by filtration. After filtration, the solvent was distilled off and the residue was vacuum dried to obtain 63.6 mg of the title compound. (Yield: 72%).

$^1$H NMR (CD$_2$Cl$_2$): δ 0.51 (6H, d, J=6.6 Hz), 1.07 (6H, d, J=7.1 Hz), 1.10 (6H, s), 2.08–2.19 (2H, m), 2.93–3.02 (2H, m), 3.34–3.39 (2H, m), 3.43–3.52 (2H, m), 6.75–6.78 (2H, m), 7.07–7.10 (2H, m), 7.35–7.40 (4H, m), 7.47–7.50 (2H, m), 7.67–7.72 (2H, m);

$^{31}$P NMR (CD$_2$Cl$_2$): δ 111.7.

Example 16

Preparation of Ru(OAc)$_2$((+)-m-ipr-BeePHOS)

60 mg of the title compound was obtained in a similar manner to Example 15 from 101.7 mg (0.232 mmol) of (+)-m-BeePHOS with 82.2 mg (0.116 mmol) of [RuCl(p-cymene)((+)-m-iPr-BeePHOS)]Cl. (Yield: 80%)

$^1$H NMR (CD$_2$Cl$_2$): δ 0.34 (3H, d, J=6.0 Hz), 1.03 (3H, J=6.6 Hz), 2.96–3.05 (1H, m), 3.28–3.34 (1H, m), 3.41–3.52 (1H, m), 6.48–6.51 (1H, m), 6.99–7.05 (1H, m), 7.22–7.52 (12H, m), 7.58–7.68 (2H, m), 7.68–7.74 (1H, m), 7.74–7.80 (1H, m);

$^{31}$P NMR (CD$_2$Cl$_2$): δ 92.4 (d, J=32.3 Hz), 111.2 (m).

USE EXAMPLE

Asymmetric Hydrogenation of Methyl N-acetamidocinnamate

A mixture of 2.3 mg(0.0029 mmol) of [Rh(cod)(+)-iPrBeePHOS]OTf, 125 mg (0.570 mmol) of methyl N-acetamidocinnamate and 1.5 ml of methanol were placed into a stainless autoclave, followed by slight heating with stirring at a hydrogen pressure of 0.4 MPa at 30° C. for 15 hours. The enantiomeric excesses (% e.e.) and conversions (%) were measured by HPLC directly, which were found to be 97.9% e.e. and >99%. The enantiomeric excesses and conversions were determined by HPLC (Daicel Chiralcel OJ, hexane: 2-propanol=90:10 (1.0 ml/min), 254 nm).

What is claimed is:

1. A phosphine compound of the formula (1):

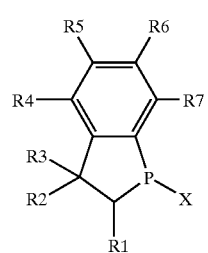

where R$^1$ is a linear or branched alkyl group having 1 to 5 carbon atoms, R$^2$ and R$^3$ represent independently a hydrogen atom or an alkyl group having 1 to 5 carbon atoms, R$^4$, R$^5$, R$^6$ and R$^7$ represent independently a hydrogen atom, a halogen atom, an alkyl group having 1 to 5 carbon atoms, an alkoxy group having 1 to 5 carbon atoms, or a dialkylamino group where the alkyl has 1 to 5 carbon atoms, X represents a functional group that forms a stable bond with phosphorous atom, with the proviso that R$^4$ and R$^5$ or R$^5$ and R$^6$ or R$^6$ and R$^7$ taken together with the carbon atoms to which they are attached optionally form a ring or fused ring.

2. A phosphine compound of the formula (2):

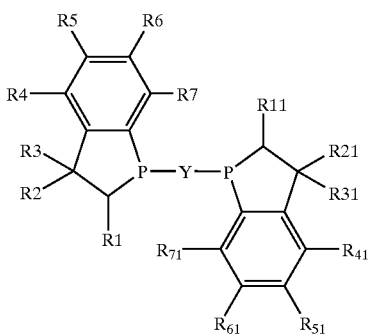

(2)

where $R^1$ is a linear or branched alkyl group having 1 to 5 carbon atoms; $R^2$ and $R^3$ represent independently a hydrogen atom or an alkyl group having 1 to 5 carbon atoms; $R^4$, $R^5$, $R^6$ and $R^7$ represent independently a hydrogen atom, a halogen atom, an alkyl group having 1 to 5 carbon atoms, an alkoxy group having 1 to 5 carbon atoms, or a dialkylamino group, where the alkyl has 1 to 5 carbon atoms, with the proviso that $R^4$ and $R^5$ or $R^5$ and $R^6$ or $R^6$ and $R^7$ taken together with the carbon atoms to which they are attached optionally form a ring or fused ring; $R^{11}$ is a linear or branched alkyl group having 1 to 5 carbon atoms, $R^{21}$ and $R^{31}$ represent independently a hydrogen atom or an alkyl group having 1 to 5 carbon atoms; $R^{41}$, $R^{51}$, $R^{61}$ and $R^{71}$ represent independently a hydrogen atom, a halogen atom, an alkyl group having 1 to 5 carbon atoms, an alkoxy group having 1 to 5 carbon atoms, a dialkylamino group, where the alkyl has 1 to 5 carbon atoms, Y represents a functional group that forms a stable bond with phosphorous atom; with the proviso that $R^{41}$ and $R^{51}$ or $R^{51}$ and $R^{61}$ or $R^{61}$ and $R^{71}$ taken together with the carbon atoms to which they are attached optionally form a ring or fused ring.

3. A transition metal complex having as a ligand, a compound as defined in claim 1.

4. A transition metal complex having as a ligand, a compound as defined in claim 2.

5. A transition metal complex comprising a complex selected from the group consisting of a rhodium complex, ruthenium complex, iridium complex, palladium complex, and nickel complex, wherein said complex has, as a ligand, a compound defined in claim 1.

6. A transition metal complex comprising a complex selected from the group consisting of a rhodium complex, ruthenium complex, iridium complex, palladium complex, and nickel complex, wherein said complex has, as a ligand, a compound defined in claim 2.

7. A catalyst for asymmetric synthesis comprising the transition metal complex according to claim 3.

8. A catalyst for asymmetric synthesis comprising the transition metal complex according to claim 4.

9. A catalyst for asymmetric synthesis comprising the transition metal complex according to claim 5.

10. A catalyst for asymmetric synthesis comprising the transition metal complex according to claim 6.

11. A catalyst for asymmetric hydrogenation comprising the transition metal complex according to claim 3.

12. A catalyst for asymmetric hydrogenation comprising the transition metal complex according to claim 4.

13. A catalyst for asymmetric hydrogenation comprising the transition metal complex according to claim 5.

14. A catalyst for asymmetric hydrogenation comprising the transition metal complex according to claim 6.

* * * * *